United States Patent [19]

Buchardt

[11] Patent Number: 4,680,399
[45] Date of Patent: Jul. 14, 1987

[54] PROCESS FOR THE ISOLATION AND PURIFICATION OF PODOPHYLLOTOXIN

[75] Inventor: Ole Buchardt, Vaerlose, Denmark

[73] Assignee: pHarma-medica a-s, Herley, Denmark

[21] Appl. No.: 773,929

[22] Filed: Sep. 9, 1985

[30] Foreign Application Priority Data

Sep. 26, 1984 [GB] United Kingdom ............... 8424269

[51] Int. Cl.$^4$ .......................................... C07D 405/14
[52] U.S. Cl. ................................. 546/139; 546/152; 546/270
[58] Field of Search ..................... 546/139, 152, 270; 548/298

[56] References Cited

U.S. PATENT DOCUMENTS 2,984,674 5/1961 Rutschmann ..................... 549/298
4,122,092 10/1978 Kende et al. ..................... 549/298

Primary Examiner—Glennon H. Hollrah
Assistant Examiner—James H. Turnipseed
Attorney, Agent, or Firm—Browdy and Neimark

[57] ABSTRACT

A process for obtaining purified podophyllotoxin from an impure podophyllotoxin containing starting material comprising forming a solution of the starting material, forming a solid complex of podophyllotoxin and an aromatic or heteroaromatic compound other than benzene, and separating the solid complex from the solution.

11 Claims, No Drawings

PROCESS FOR THE ISOLATION AND PURIFICATION OF PODOPHYLLOTOXIN

The invention relates to a new method for the isolation and purification of podophyllotoxin from relatively impure sources thereof, particularly plant extracts, for example resins obtained by extraction from plants of the genus podophyllum.

Podophyllotixin is a highly biologically active substance which is particularly useful as a drug against condylomata acuminata (veneral warts) [G. Gabriel and R. N. T. Thin, Br.J.Vener.Dis., 59, 124–126 (1983) as well as possessing cytostatic [G. von Krogh and H. I. Maibach, Dermatologica, 167, 70–77 (1983)] and antiviral properties [T. Markkanen, M. L. Makinen, J. Miettinen, E. Maunuksela, T. Laijoki and J. Paranko, Drugs Exp.Clin.Res. 9, 1–7 (1983)].

Previously, podophyllotoxin has been isolated from the above-mentioned resins by various laborious procedures, all of which included solvent extraction, as a rule with chloroform, followed by further processing steps. According to the most authoritative newer literature [W. M. Hearon and W. S. MacGregor, Chem.Rev., 55, 1002 (1955); J. L. Hartwell and W. E. Detty, J.Am.-Chem.Soc., 246–253 (1950)] chromatographic purification was necessary in order to obtain podophyllotoxin. In many cases, benzene has been used in the course of the purification procedures despite the acknowledged health hazards which arise. Furthermore, chromatography has previously been regarded as being absolutely essential in order to obtain podophyllotoxin, i.e. a degree of purity such that the podophyllotoxin is only slightly contaminated with the many congeners which exist in the plant material. This has resulted in pure podophyllotoxin being a rare and expensive substance which is difficult to obtain in large amounts.

There is recently been a heightened demand for pure podophyllotoxin, both as a raw material for conversion to various pharmacologically active derivatives and in clinical treatments using podophyllotoxin itself. In both cases it is highly desirable to use as pure a product as possible.

According to one aspect, the present invention provides a process for obtaining purified podophyllotoxin from a solution thereof which comprises forming a solid complex of podophyllotoxin and an aromatic or heteroaromatic compound other than benzene and separating the solid complex from the solution.

The process of the invention, according to one aspect, is well suited for the purification of podophyllotoxin in large quantities, it avoids the strongly carcinogenic solvent benzene, and it gives a very high yield of pure podophyllotoxin.

The process of the invention is based on the previously unknown ability of podophyllotoxin to form complexes with a large variety of aromatic and heteroaromatic, compounds, including phenol, toluene, chlorobenzene, anisole, o-, m- and p-xylenes and nitrobenzene, and basic substances such as aniline and pyridine, and homologues thereof such as naphthalene, quinoline and isoquinoline. Furthermore, it avoids the need to purify the crude resin by solvent extraction.

The present invention also provides a process for obtaining purified podophyllotoxin from a solution thereof which comprises (a) forming a solid complex of podophyllotoxin and an aromatic or heteroaromatic compound, (b) separating the complex from the solution, (c) forming a solution comprising podophyllotoxin from said separated complex, (d) forming a solid complex of podophyllotoxin from the solution of step (c) and an aromatic or heteroaromatic compound, and (e) separating the solid complex formed in step (d) from the solution, wherein the aromatic or heteroaromatic compounds used in steps (a) and (d) are different.

The precise condition for carrying out the methods of the invention are not critical and can be varied a great deal, but the general principle consists of dissolving impure podophyllotoxin, for example podophyllum resin in a suitable solvent, preferably a solvent in which the entire resin is soluble, for example a $C_{1-3}$ lower aliphatic alcohol or a $C_{1-3}$ lower alkyl carboxylic acid ester. To the solution is then added the complexing aromatic compound, and if required this may be followed by various amounts of water. This causes precipitation of generally well-crystalline complexes which may be isolated, and which after removal of the complexing agent can give about 90% of pure podophyllotoxin in high yield. By repetition of this procedure wth various complexing agents, 92–95% pure podophyllotoxin can be obtained. It is often found that several of its congeners remain as persistent impurities, even after as many as 5–8 recrystallizations using various solvents and complexing agents and to achieve an even higher degree of purity a further process step (which itself forms a further aspect of the present invention) may be employed.

Thus according to the invention, in a preferred embodiment thereof, which enables podophyllotoxin of especially high purity to be obtained "absolute" purification can be performed in a very surprising and unforeseeable manner, namely by extraction of a solution of the impure podophyllotoxin in a water-immiscible solvent, for example chloroform, with aqueous base. This result is surprising because according to the literature, podophyllotoxin is very labile under basic conditions, being transformed into its epimer, picropodophyllin when treated with alkali [W, Borsche and J. Niemann, Liebiegs Ann.Chem. 494, 126–142 (1932)].

The following Examples illustrate the process of the invention.

EXAMPLE 1

A. Podophyllin (643 g) is dissolved in ethanol (1.5 l) with gentle heating. To the hot solution is added toluene (643 ml) followed by water (129 ml). The solution is cooled with ice-water and the precipitated crystalline material isolated by filtration and washed with ether (2 l). Yield: 342.8 g.

This material is a complex of podophyllotoxin, toluene and water, and it was shown by HPLC to contain ca. 13% of related lignans.

The complex was redissolved in ethanol (1.0 l) with gentle heating, pyridine (140 ml) followed by water (470 ml) were added, and the solution was cooled with ice-water. The precipitated crystalline material was isolated by filtration and washed with ether (250 ml). Yield: 292 g.

This material consists of a podophyllotoxin-pyridine-water complex which was shown by HPLC to contain ca. 7% of other related lignans. The material was recrystallized from ethanol (1.0 l)-water (430 ml) to give 239 g of the pyridine-water complex.

B. The complex (119 g) was dissolved in chloroform (1.2 l) which was treated with: (i) 0.8N HCl (500 ml), (ii) 0.4N NaOH (500 ml), (iii) 0.01N HCl (450 ml), (iv) water (450 ml), and (v) saturated aqueous sodium chloride (500 ml).

The chloroform solution was dried over solid magnesium sulfate, the chloroform was removed, in vacuo, and the remaining sirupy material was recrystallized from ethyl acetate (450 ml) to give podophyllotoxin, aq. (50 g). This material was shown by HPLC to contain <0.4% of other lignans. A sample was subjected to drying (100° C.), in vacuo, to give analytically pure podophyllotoxin. Anal. Found (cal.) C 63.62 (63.76), H 5.39 (5.35). Its IR, $^1$HNMR and $^{13}$C NMR spectra were identical with those recorded in the literature.

EXAMPLE 2

A. Podophyllin (1 kg) was dissolved in ethanol (3 l) with gentle heating. As soon as the solution was homogeneous, toluene (1.0 l) and water (200 ml) were added and the mixture was cooled with ice-water. The precipitated crystalline material was filtered off, and washed with ether (1.0 l). This was subsequently recrystallized from ethanol (2 l), toluene (650 ml) and water (130 ml). The isolated crystalline material was redissolved in ethanol (1.5 l), pyridine (210 ml) and water (630 ml) were added, and the solution was cooled with ice-water. The precipitated crystalline complex was isolated, washed with ether (1.0 l) and dried to give 478 g of material.

The product of 2A was dissolved in chloroform (5 l) and treated with: (i) 0.4N HCl (2 l), (ii) 0.2N NAOH (2 l), (iii) 0.03N HCl (1.4 l) (iv) saturated aqueous sodium chloride (700 ml), and (v) dried over magnesium sulfate. The chloroform was removed, in vacuo, and the remaining sirupy material recrystallized from ethanol-water (1.4 l–0.9 l). This yielded podophyllotoxin, 2H$_2$O (419 g, ~39%) which contained <0.6% picropodophyllin and <0.1% of other related lignans.

Anal. Found (calc.) C 58.63 (58.67), H 5.53 (5.77). Identified by IR and $^1$HNMR spectroscopy. A small sample was dried (100° C.), in vacuo, to give an analytically pure sample. Anal. C 63.75 (63.76), H 5.41 (5.35).

EXAMPLE 3

A. Podophyllin (500 g) was dissolved in ethanol (1.5 l) with gentle heating, toluene (0.5 l) and water 100 ml) were added, the solution was cooled, and the precipitated crystalline material was isolated by filtration and washed with ethanol-toluene-water (15:5:1, 200 ml). This was immediately redissolved in ethanol (1.0 l), toluene (330 ml) and water (66 ml), and the solution was cooled with ice-water. The precipitate was isolated as described above and dried to give 211 g. This was redissolved in boiling methanol (500 ml) and the hot solution was filtered, water (368 ml) was added, and the solution was cooled with ice-water to give after filtration and drying, in vacuo, over H$_2$SO$_4$, and at ambient pressure at 100° C., 192 g of podophyllotoxin and other related lignans in a ratio of 9:1.

B. The above impure podophyllotoxin (5 g) was dissolved in chloroform (50 ml) and treated successively with: (i) 0.4N NaOH (50 ml), (ii) 0.01N HCl (50 ml), (iii) water (50 ml), (iv) saturated sodium chloride (50 ml), the chloroform was removed, in vacuo, and the remaining material was recrystallized from ethanol-water (1:1, 20 ml). This gave podophyllotoxin, aq., identified by IR spectroscopy which contained <1.4% of other lignans.

EXAMPLE 4

A. Podophyllin (50 g) was dissolved in ethanol (150 ml) with heating, followed by addition of chlorobenzene (50 ml) and water (10 ml). After cooling, the precipitate was isolated by filtration and washed with ether (20 ml). Yield of podophyllin-chlorobenzene-water complex: 19.5 g, which was shown to contain ca. 13% of other lignans.

The above material (5 g) was redissolved in ethanol (15 ml), phenol (5 g) and water (2 ml) were added, the solution was cooled, and the precipitated material was removed by filtration and washed with ether (10 ml). Yield of podophyllotoxin-phenol-water complex: 4.2 g.

B. This was dissolved in ethyl acetate (20 ml) and the solution was treated with 2N NaOH (20 ml). The organic phase was separated and concentrated, in vacuo. The resulting material was recrystallized from ethanol-water (1:1, 20 ml) to give, after drying, in vacuo, over H$_2$SO$_4$: 3.75 g of >98.5% pure podophyllotoxin, aq., determined by HPLC and identified by IR, $^1$H NMR and $^{13}$C NMR spectroscopy, $[\alpha]_D^{20} = -118.5°$.

The following example illustrates the results of using various combinations of complexing agents in Step A.

EXAMPLE 5

General procedure: Podophyllin (60 g) was dissolved by gentle heating in a suitable solvent (180 ml). In some cases a residue remained, in which case the solution was decanted off. This was followed by addition of an aromatic complexing agent (60 ml, or 60 g if a solid) followed by addition of various amounts of water. After cooling, the precipitated complex was isolated, and the procedure repeated with the same, or other solvents and complexing agents. The isolated material was eventually recrystallized, and the complexing agents removed, and in each case identified by IR spectroscopy and/or HPLC analysis. The results are shown in Table 1.

TABLE 1

Isolation of Podophyllotoxin from Podophylline

| Podophyllotoxin Purity in % | Podophylline g | First Crystallization Solvent ml | Complexing agent ml | Water ml | Second Crystallization Solvent ml | Complexing agent ml | Water ml | Third Crystallization Solvent ml | Complexing agent ml | Water ml | Yield g |
|---|---|---|---|---|---|---|---|---|---|---|---|
| 90.5 | 10 | EtOH,30 | Toluene,10 | 2 | EtOH,30 | Toluene,6 | — | MeOH,17 | — | 14 | 5.5 |
| 91.4 | 10 | EtOH,30 | Toluene,10 | 2 | EtOH,30 | o-Xylene,6 | — | MeOH,15 | — | 15 | 4.3 |
| 91.0 | 10 | EtOH,30 | Toluene,10 | 2 | EtOH,30 | m-Xylene,6 | — | MeOH,16 | — | 11 | 4.7 |
| 92.3 | 10 | EtOH,30 | Toluene,10 | 2 | EtOH,30 | p-Xylene,6 | — | MeOH,17 | — | 10 | 5.0 |
| 90.2 | 10 | EtOH,30 | Toluene,10 | 2 | EtOH,30 | Anisole,6 | — | MeOH,17 | — | 10 | 5.0 |
| 91.7 | 10 | EtOH,30 | Toluene,10 | 2 | EtOH,30 | Chlorobenzene,6 | — | MeOH,17 | — | 15 | 4.9 |
| 92.7 | 8.3 | EtOH,25 | o-Xylene,10 | 2 | EtOH,25 | Toluene,4.3 | 0.85 | MeOH,17 | — | 10 | 3.1 |
| 92.8 | 8.3 | EtOH,25 | o-Xylene,10 | 2 | EtOH,25 | o-Xylene,4.3 | 0.85 | MeOH,12 | — | 10 | 3.1 |

TABLE 1-continued

Isolation of Podophyllotoxin from Podophylline

| Podophyllotoxin Purity in % | Podophylline g | First Crystallization Solvent ml | First Crystallization Complexing agent ml | Water ml | Second Crystallization Solvent ml | Second Crystallization Complexing agent ml | Water ml | Third Crystallization Solvent ml | Third Crystallization Complexing agent ml | Water ml | Yield g |
|---|---|---|---|---|---|---|---|---|---|---|---|
| 93.8 | 8.3 | EtOH,25 | o-Xylene,10 | 2 | EtOH,25 | m-Xylene,4.3 | 0.85 | MeOH,27 | — | 27 | 3.1 |
| n.d. | 8.3 | EtOH,25 | o-Xylene,10 | 2 | EtOH,25 | p-Xylene,4.3 | 0.85 | MeOH,15 | — | 10 | 3.4 |
| 92.7 | 8.3 | EtOH,25 | o-Xylene,10 | 2 | EtOH,25 | Anisole,4.3 | 0.85 | MeOH,15 | — | 10 | 3.3 |
| 92.5 | 8.3 | EtOH,25 | o-Xylene,10 | 2 | EtOH,25 | Chlorobenzene,4.3 | 0.85 | MeOH,15 | — | 20 | 3.2 |
| 92.1 | 10 | EtOH,30 | m-Xylene,10 | 2 | EtOH,25 | Toluene,5 | 1.2 | MeOH,15 | — | 10 | 3.7 |
| 91.5 | 10 | EtOH,30 | m-Xylene,10 | 2 | EtOH,25 | o-Xylene,6 | 1.2 | MeOH,15 | — | 11 | 3.5 |
| 92.3 | 10 | EtOH,30 | m-Xylene,10 | 2 | EtOH,25 | m-Xylene,6 | 1.2 | MeOH,25 | — | 20 | 4.1 |
| 91.5 | 10 | EtOH,30 | m-Xylene,10 | 2 | EtOH,25 | p-Xylene,6 | 1.2 | MeOH,25 | — | 20 | 4.1 |
| 92.7 | 10 | EtOH,30 | m-Xylene,10 | 2 | EtOH,25 | Anisole,6 | 1.2 | MeOH,25 | — | 20 | 4.2 |
| 92.6 | 10 | EtOH,30 | m-Xylene,10 | 2 | EtOH,25 | Chlorobenzene,6 | 1.2 | MeOH,25 | — | 20 | 3.8 |
| 91.8 | 10 | EtOH,30 | p-Xylene,10 | 2 | EtOH,30 | Toluene,5 | 1.0 | MeOH,25 | — | 20 | 4.5 |
| 91.5 | 10 | EtOH,30 | p-Xylene,10 | 2 | EtOH,30 | o-Xylene,5 | 1.0 | MeOH,25 | — | 20 | 4.5 |
| 93.9 | 10 | EtOH,30 | p-Xylene,10 | 2 | EtOH,30 | m-Xylene,5 | 1.0 | MeOH,25 | — | 20 | 4.7 |
| 92.6 | 10 | EtOH,30 | p-Xylene,10 | 2 | EtOH,30 | p-Xylene,5 | 1.0 | MeOH,25 | — | 20 | 3.9 |
| 91.3 | 10 | EtOH,30 | p-Xylene,10 | 2 | EtOH,30 | Anisole,5 | 1.0 | MeOH,25 | — | 20 | 4.7 |
| 91.9 | 10 | EtOH,30 | p-Xylene,10 | 2 | EtOH,30 | Chlorobenzene,5 | 1.0 | MeOH,25 | — | 20 | 1.9 |
| 92.5 | 10 | EtOH,30 | Anisole,10 | 2 | EtOH,30 | Toluene,5 | 1.0 | MeOH,25 | — | 20 | 3.8 |
| 92.7 | 10 | EtOH,30 | Anisole,10 | 2 | EtOH,30 | o-Xylene,5 | 1.0 | MeOH,25 | — | 20 | 3.4 |
| 94.9 | 10 | EtOH,30 | Anisole,10 | 2 | EtOH,30 | m-Xylene,5 | 1.0 | MeOH,25 | — | 20 | 3.7 |
| 93.0 | 10 | EtOH,30 | Anisole,10 | 2 | EtOH,30 | p-Xylene,5 | 1.0 | MeOH,25 | — | 20 | 3.7 |
| 92.3 | 10 | EtOH,30 | Anisole,10 | 2 | EtOH,30 | Anisole,5 | 1.0 | MeOH,25 | — | 20 | 3.7 |
| 93.1 | 10 | EtOH,30 | Anisole,10 | 2 | EtOH,30 | Chlorobenzene,5 | 1.0 | MeOH,25 | — | 20 | 3.9 |
| 90.7 | 10 | EtOH,30 | Chlorobenzene,10 | 2 | EtOH,30 | Toluene,5 | 1.0 | MeOH,25 | — | 20 | 2.7 |
| 92.8 | 10 | EtOH,30 | Chlorobenzene,10 | 2 | EtOH,30 | o-Xylene,5 | 1.0 | MeOH,25 | — | 20 | 3.1 |
| 93.8 | 10 | EtOH,30 | Chlorobenzene,10 | 2 | EtOH,30 | p-Xylene,5 | 1.0 | MeOH,25 | — | 20 | 2.7 |
| 92.1 | 10 | EtOH,30 | Chlorobenzene,10 | 2 | EtOH,30 | Anisole,5 | 1.0 | MeOH,25 | — | 20 | 3.0 |
| 93.0 | 10 | EtOH,30 | Chlorobenzene,10 | 2 | EtOH,30 | Chlorobenzene,5 | 1.0 | MeOH,25 | — | 20 | 2.6 |
| 93.2 | 10 | EtOH,30 | Toluene,10 | 2 | — | — | — | ClCH$_2$CH$_2$Cl,25 | — | — | 3.3 |
| 94.5 | 10 | EtOH,30 | Toluene,10 | 2 | — | — | — | EtOAc,30 | — | — | 3.5 |
| 89.0 | 10 | EtOH,30 | Toluene,10 | 2 | — | — | — | 1-Hexanol,30 | — | — | 4.2 |
| 89.5 | 10 | EtOH,30 | Toluene,10 | 2 | — | — | — | 2-Propanol,30 | — | — | 1.9 |
| 92.9 | 10 | EtOH,30 | Toluene,10 | 2 | — | — | — | Ethanol,20 | — | — | 2.8 |
| 91.0 | 10 | EtOH,30 | Toluene,10 | 2 | EtOH,15 | Toluene,1.5 | — | — | — | — | 4.6 |
| 90.5 | 10 | EtOH,30 | Toluene,10 | 2 | MeOH,20 | — | — | — | — | — | 3.0 |
| 91.3 | 10 | EtOH,30 | Toluene,10 | 2 | EtOH,20 | Toluene,815 mg | — | — | — | — | 3.7 |
| 92.0 | 10 | EtOH,30 | Toluene,10 | 2 | EtOH,15 | Phenol,2 g | — | MeOH,15 | — | 15 | 2.6 |
| 93.5 | 10 | EtOH,30 | Toluene,10 | 2 | EtOH,15 | Pyridine,2 g | — | MeOH,15 | — | 15 | 3.9 |
| 94.5 | 10 | EtOH,30 | Toluene,10 | 2 | EtOH,15 | Nitrobenzene,2 g | — | MeOH,15 | — | 15 | 3.0 |
| 93.4 | 10 | EtOH,30 | o-Xylene,5 | 2 | EtOH,20 | m-Xylene,4 (followed by treatment with boiling decaline) | 0.9 | EtOH,10 | — | — | 1.5 |
| 93.0 | 10 | EtOH,30 | Toluene,10 | 2 | EtOH,20 | Benzyl Alcohol,5 | 1.0 | EtOH,10 | — | 10 | 3.7 |
| 91.8 | 10 | EtOH,30 | Toluene,10 | 2 | EtOAc,20 | Toluene,2 | — | — | — | — | 2.9 |
| 92.8 | 10 | EtOH,30 | Toluene,10 | 2 | MeOH,20 | Toluene,2 | 1.0 | — | — | — | 3.8 |
| n.d. | 10 | MeOH,30 | Toluene,10 | 2 | MeOH,30 | Toluene,10 | 2.0 | — | — | — | 3.8 |
| n.d. | 10 | EtOH,30 | Nitrobenzene,12 | 11 | EtOH,15 | Pyridine,5 | 6.0 | — | — | — | 4.0 |
| 91.3 | 10 | EtOH,30 | Toluene,10 | 2 | EtOH,15 | Aniline,5 | 4.0 | — | — | — | 3.2 |
| n.d. | 10 | EtOH,30 | Benzene,10 | 2 | EtOH,15 | Benzene,5 | 1.0 | — | — | — | 3.9 |
| n.d. | 10 | 1-Butanol,30 | Toluene,10 | 2 | Butanol,15 | Toluene,5 | 1.0 | — | — | — | 4.6 |
| n.d. | 10 | EtOAc,30 | Toluene,10 | 2 | EtOAc,30 | Toluene,5 | 1.0 | — | — | — | 3.4 |
| n.d. | 10 | EtOH,30 | Isoquinoline,10 | 15 | EtOH,8 | Toluene,2.5 | 0.5 | — | — | — | 2.4 |
| n.d. | 10 | Dioxane,30 | Toluene,10 | 2 | Dioxane,9 | Toluene,3 | 0.6 | — | — | — | 2.2 |
| n.d. | 10 | Acetone,30 | Toluene,10 | 2 | Acetone,9 | Toluene,3 | 0.6 | — | — | — | 2.3 |
| n.d. | 10 | Acetonitrile,30 | Toluene,10 | 2 | Acetonitrile,11 | Toluene,3.5 | 0.7 | — | — | — | 2.5 |
| n.d. | 10 | Chloroform,30 | Toluene,10 | 2 | Chloroform,14 | Toluene,4.8 | 1.0 | — | — | — | 3.5 |
| n.d. | 10 | ClCH$_2$CH$_2$Cl,30 | Toluene,10 | 2 | ClCH$_2$CH$_2$Cl,11 | Toluene,3.8 | 0.8 | — | — | — | 1.3 |
| n.d. | 10 | Toluene,30 | — | 2 | Toluene,9 | — | 0.6 | — | — | — | 1.2 |

I claim:

1. In a process for obtaining purified podophyllotoxin from an impure podophyllotoxin containing starting material, the improvement comprising forming a solution of said starting material, forming a solid complex of podophyllotoxin and an aromatic or heteroaromatic compound other than benzene, and separating the solid complex from the solution.

2. A process according to claim 1 wherein the solid complex comprises podophyllotoxin, said aromatic or heteroaromatic compound and water.

3. A process according to claim 1 wherein the solvent for the solution comprises ethanol.

4. A process according to claim 1 wherein the complex is formed by adding said aromatic or heteroaromatic compound and water to the solution of said starting material.

5. A process according to claim 1 wherein a solution is formed by dissolving the separated complex in a solvent and the step of forming a solid complex of podophyllotoxin, an aromatic or heteroaromatic compound and optionally water and separating the solid complex from the solution is repeated.

6. A process according to claim 5 wherein different aromatic or heteroaromatic compounds are used in at least two successive stages.

7. A process for obtaining purified podophyllotoxin from a solution thereof which comprises (a) forming a solid complex of podophyllotoxin and an aromatic or heteroaromatic compound and optionally water, (b) separating the complex from the solution, (c) forming a solution comprising podophyllotoxin from said separated complex, (d) forming a solid complex of podophyllotoxin from the solution of step (c) and an aromatic or heteroaromatic compound and optionally water, (e) separating the solid complex formed in step (d) from the solution, (f) isolating podophyllotoxin in free form from the separated complex, wherein the aromatic or heteroaromatic compounds used in steps (a) and (d) are different.

8. A process according to claim 1 wherein the aromatic or heteroaromatic compounds used are selected from toluene, o-xylene, m-xylene, p-xylene, anisole, chlorobenzene, pyridine, phenol, nitrobenzene, quinoline, isoquinoline, furfuryl alcohol and naphthalene.

9. A process according to claim 1 in which the resulting product is subjected to a further purification step comprising contacting a solution thereof in a water-immiscible solvent with an aqueous base.

10. A process for removing impurities from a solution comprising impure podophyllotoxin and a water-immiscible organic solvent which comprises contacting the solution with an aqueous base.

11. A process according to claim 10 wherein the base is an alkali metal hydroxide.

* * * * *